United States Patent
Durand

(10) Patent No.: US 11,426,305 B2
(45) Date of Patent: Aug. 30, 2022

(54) SYSTEMS AND METHODS FOR OBSTRUCTIVE SLEEP APNEA DETECTION AND MONITORING

(71) Applicant: Case Western Reserve University, Cleveland, OH (US)

(72) Inventor: Dominique M. Durand, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 406 days.

(21) Appl. No.: 16/488,947

(22) PCT Filed: Feb. 28, 2018

(86) PCT No.: PCT/US2018/020183
§ 371 (c)(1),
(2) Date: Aug. 27, 2019

(87) PCT Pub. No.: WO2018/160670
PCT Pub. Date: Sep. 7, 2018

(65) Prior Publication Data
US 2019/0380864 A1 Dec. 19, 2019

Related U.S. Application Data

(60) Provisional application No. 62/567,358, filed on Oct. 3, 2017, provisional application No. 62/516,863, filed on (Continued)

(51) Int. Cl.
| | | |
|---|---|---|
| A61F 5/56 | (2006.01) | |
| A61B 5/08 | (2006.01) | |
| A61B 5/00 | (2006.01) | |

(52) U.S. Cl.
CPC ............ *A61F 5/566* (2013.01); *A61B 5/0826* (2013.01); *A61B 5/682* (2013.01)

(58) Field of Classification Search
CPC ... A61F 5/56; A61F 5/566; A61B 5/08; A61B 5/0826; A61B 5/48; A61B 5/4806;
(Continued)

(56) References Cited

U.S. PATENT DOCUMENTS 8,249,723 B2 * 8/2012 McCreery ................ A61B 5/11
607/134
9,204,991 B1 * 12/2015 Harkins ................. A61F 5/566
(Continued)

FOREIGN PATENT DOCUMENTS

| DE | 19501363 A1 | 9/1995 |
|---|---|---|
| DE | 10240725 A1 | 3/2004 |

OTHER PUBLICATIONS

Mayo Clinic, "Obstructive sleep apnea" Diagnosis, 1998-2020 Mayo Foundation for Medical Education and Research, last accessed Feb. 13, 2020, http://www.mayoclinic.org/diseases-conditions/obstructive-sleep-apnea/diagnosis-treatment/diagnosis/dxc-20206026.
(Continued)

*Primary Examiner* — Michelle J Lee
(74) *Attorney, Agent, or Firm* — Tarolli, Sundheim, Covell & Tummino LLP

(57) ABSTRACT

One aspect of the present disclosure relates to a system that monitors and detects obstructive sleep apnea (OSA). The system includes an oropharynx protection appliance (12), which includes a passive tongue retention structure (13) having an end portion adapted to prevent a pharyngeal portion of a tongue of a subject from collapsing and at least one anchoring structure (15) that is connected to the passive tongue retention structure and adapted to secure the passive tongue retention structure within the subject's mouth in a removable fashion. The system also includes a sensing system (14) attached to a portion of the oropharynx apparatus. The sensing system includes a sensor (16) to measure
(Continued)

a position of the pharyngeal portion of the tongue to detect an obstruction of the oropharynx; and a wireless transceiver (17) to transmit data related to the obstruction of the oropharynx to a remote diagnostic device (18).

17 Claims, 13 Drawing Sheets

Related U.S. Application Data on Jun. 8, 2017, provisional application No. 62/464,702, filed on Feb. 28, 2017.

(58) Field of Classification Search
CPC ....... A61B 5/4818; A61B 5/68; A61B 5/6801; A61B 5/6813; A61B 5/682; A61B 5/11; A61B 5/1107; A61B 5/113; A61C 7/00; A61C 7/08; A61C 7/36; A61N 1/18; A61N 1/32; A61N 1/36; A61N 1/3601
See application file for complete search history.

(56) References Cited

U.S. PATENT DOCUMENTS

| | | |
|---|---|---|
| 2001/0027793 A1 | 10/2001 | Tielemans |
| 2008/0223367 A1 | 9/2008 | Cox et al. |
| 2012/0118297 A1 | 5/2012 | Barodka |
| 2017/0087360 A1* | 3/2017 | Scheiner ............ A61N 1/36139 |
| 2018/0125701 A1* | 5/2018 | Hadas ..................... A61C 7/36 |
| 2019/0274871 A1* | 9/2019 | Veis ........................ A61F 5/566 |

OTHER PUBLICATIONS

PCT International Search Report and Written Opinion for corresponding International Application Serial No. PCT/US2018/020183, dated Jun. 7, 2018, pp. 1-15.

\* cited by examiner

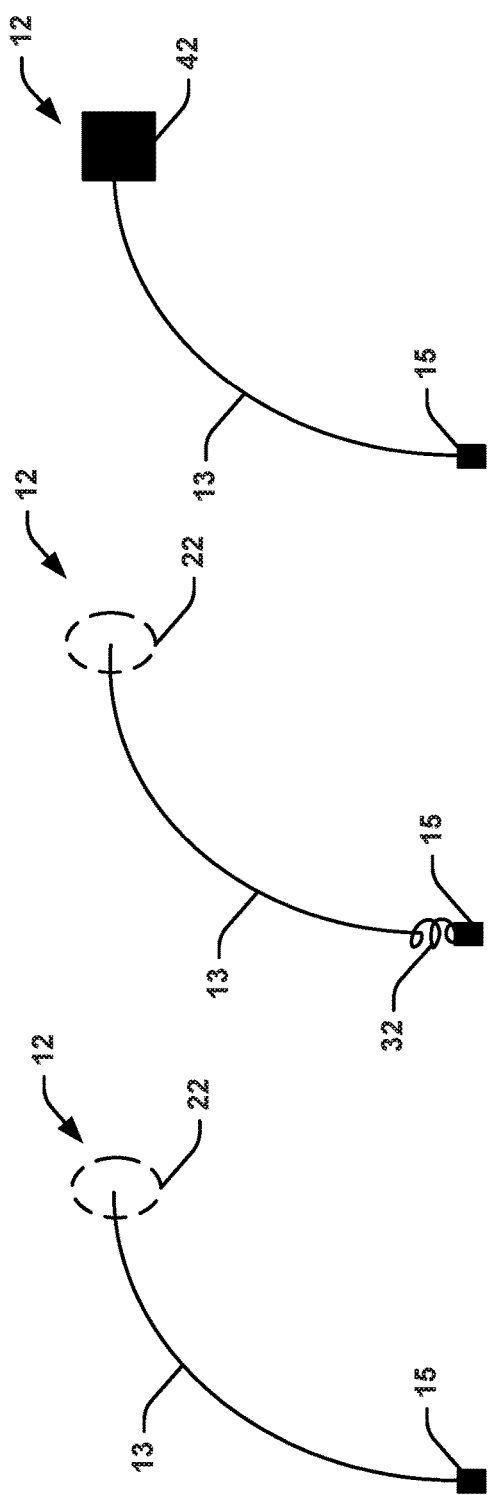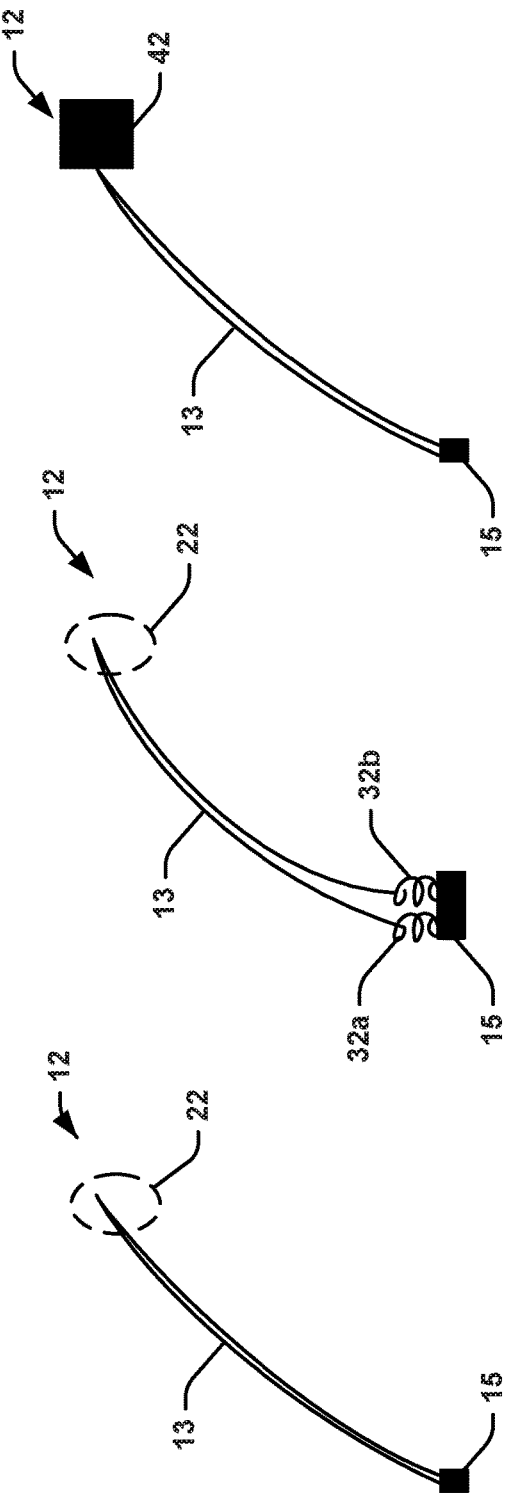

SYSTEMS AND METHODS FOR OBSTRUCTIVE SLEEP APNEA DETECTION AND MONITORING

CROSS-REFERENCE TO RELATED APPLICATIONS

This application claims the benefit of U.S. Provisional Application No. 62/567,358, filed Oct. 3, 2017, entitled "SYSTEMS AND METHODS FOR OBSTRUCTIVE SLEEP APNEA DETECTION AND MONITORING". This application also claims the benefit of U.S. Provisional Application No. 62/464,702, filed Feb. 28, 2017, entitled "TONGUE RETENTION PROSTHESIS FOR OBSTRUCTIVE SLEEP APNEA" and U.S. Provisional Application No. 62/516,863, filed Jun. 8, 2017, entitled "OROPHARYNX PROTECTION APPLIANCE." These provisional applications are hereby incorporated by reference in their entirety for all purposes.

TECHNICAL FIELD

The present disclosure relates generally to obstructive sleep apnea (OSA) and, more specifically, to systems and methods for OSA detection and monitoring.

BACKGROUND

Sleep apnea is a sleep disorder in which a sufferer has trouble breathing during sleep. This trouble breathing during sleep can lead to nocturnal hypoxemia and sleep fragmentation, which can lead to co-morbidities, like daytime sleepiness, as well as cardiac and neural complications. The most common type of sleep apnea is obstructive sleep apnea (OSA), affecting 27 million patients in the US alone. OSA is characterized by the recurrent collapse of soft tissue obstructing the upper airway during sleep. Such airway obstructions have been attributed, in part, to a collapse of the soft tissue structures surrounding the upper airway into the airway when the throat and tongue muscles relax during sleep. These airway obstructions are dangerous, leading to pauses in breathing or instances of shallow or infrequent breathing.

The frequent airway obstructions experienced by individuals suffering from OSA can negatively impact such individuals' health and quality of life. While no drug therapies exist to treat sleep apnea, several mechanical therapies exist, such as continuous positive airway pressure (CPAP) therapy or a mandibular advancement device (MAD) treatment. However, individuals with OSA are rarely aware of their difficulty breathing, even upon awakening, leading to the associated poor diagnosis and treatment. Even when an individual suspects OSA, current techniques for diagnosis, like polysomnography, are expensive and require an overnight stay in a sleep lab. Furthermore, while polysomnography measures various symptoms of OSA, like oxygen saturation, respiration, chest movements during sleep, and sleep patterns, polysomnography does not provide a direct measure of airway obstruction.

SUMMARY

The present disclosure relates generally to obstructive sleep apnea (OSA) and, more specifically, to systems and methods for OSA detection and monitoring. For example, the systems and methods can track movement of a subject's tongue during sleep to determine the amount and duration of airway obstruction that are indicative of OSA. As another example, the systems and methods can also monitor additional properties associated with OSA, including air flow, force, oxygen saturation ($SaO_2$), electrocardiogram (ECG), temperature, and/or sound.

In one aspect, the present disclosure includes a system that tracks obstruction of the oropharynx. The system includes an oropharynx protection appliance, which is made of a passive tongue retention structure having an end portion adapted to prevent a pharyngeal portion of a tongue of a subject from collapsing and at least one anchoring structure that is connected to the passive tongue retention structure and adapted to secure the passive tongue retention structure within the subject's mouth in a removable fashion. The system also includes a sensing system attached to a portion of the oropharynx apparatus. The sensing system includes a sensor to measure a position of the pharyngeal portion of the tongue to detect an obstruction of the oropharynx; and a wireless transceiver to transmit data related to the obstruction of the oropharynx to a remote diagnostic device.

In another aspect, the present disclosure includes a method for tracking obstruction of the oropharynx. The method can include measuring, by a sensor of a sensing system attached to a portion of an oropharynx apparatus, a position of the pharyngeal portion of a tongue of a subject during sleep. Data related to the position of the pharyngeal portion of the tongue can be transmitted, by a wireless transceiver, to an external diagnostic device. The method can also include determining, by the external diagnostic device, a degree of obstruction of the oropharynx at one or more times during sleep based on the transmitted data.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 4-14 are illustrations of various examples of the oropharynx appliance of FIG. 1;

DETAILED DESCRIPTION

I. Definitions

Figure 1:
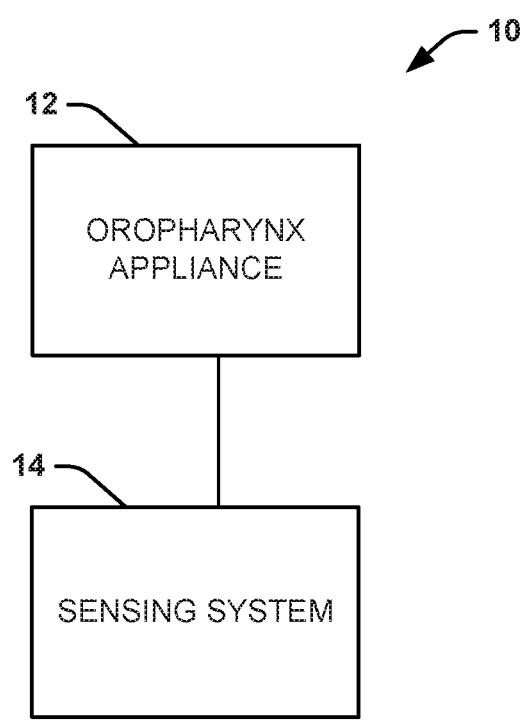
FIG. 1 is an illustration of a system that detects and monitors obstructive sleep apnea (OSA), in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

As used herein, the terms "first," "second," etc. are not meant to be limiting, instead, these terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the terms "obstructive sleep apnea" and "OSA" can refer to a sleep disorder that is caused by complete or partial obstruction of a subject's airway, leading to repetitive episodes of shallow or paused breathing during sleep, despite the subject's effort to breathe.

As used herein, the term "obstruction" can refer to something that impedes or prevents passage. For example, an obstruction in the oropharynx can prevent the passage of air through the oropharynx. The obstruction of the oropharynx can be due to a collapse of soft tissue of the subject's upper airway into the oropharynx.

As used herein, the term "sleep" can refer to a period of rest of a patient's body and mind during which consciousness is partially or completely suspended and bodily functions are partially suspended.

As used herein, the term "detection" can refer to the action or process of identifying or revealing the presence of something that is normally concealed. For example, symptoms related to the presence of OSA can be detected in a patient, including airway obstruction, air flow, force, oxygen saturation ($SaO_2$), electrocardiogram (ECG), sound, and the like. In some instances, the detection can be performed by one or more sensors.

As used herein, the term "sensor" can refer to a device that detects or measures a physical property and records, indicates, or otherwise responds to the physical property.

As used herein, the term "diagnosis" can refer to an identification of the nature of an illness or other problem through examination of the symptoms.

As used herein, the term "diagnostic" can refer to one or more devices that can examine physical properties of symptoms and create data related to a diagnosis of an illness or other problem.

As used herein, the term "oral cavity" can refer to the cavity of the mouth, bounded by the upper and lower jawbones and the cheeks.

As used herein, the term "mouth" can refer to the structures enclosing or being within the oral cavity. The mouth can include a plurality of teeth and a tongue. The mouth can also include gums and tissue surrounding the upper and lower jawbones.

As used herein, the term "mandible" can refer to a subject's lower jawbone. In some instances, the mandible can also refer to at least a portion of the tissue within the mouth surrounding the lower jawbone. Notably, the lower jawbone is the only moveable bone in the skull.

As used herein, the term "tongue" can refer to the fleshy muscular organ in a subject's mouth. The tongue can be composed of an anterior oral part and a posterior pharyngeal part. The posterior pharyngeal part can be the posterior third of the tongue that is part of the oropharynx.

As used herein, the term "pharynx" can refer to a membrane-lined cavity behind the nose and mouth, connecting the nose and mouth to the esophagus.

As used herein, the term "oropharynx" can refer to a part of pharynx generally lying behind the mouth between the soft palate and the hyoid bone. The oropharynx begins where the oral cavity stops and includes the posterior pharyngeal part of the tongue.

As used herein, the term "wire" can refer to a metal, polymer, composite, or other material structure. In some instances, the diameter of the material structure can be constant. In other instances, the diameter of the material structure can be variable in at least a portion of the wire. The cross section of the wire can be circular, rectangular, flat, star, or any other shape.

As used herein, the term "arcuate" can refer to a generally curved shape. Examples of arcuate shapes include an arc or a bow. However, in some instances, the arcuate shape can include one or more bent portions as long as the general curvature exists.

As used herein, the term "spring" can refer to a resilient device that can be pressed or pulled but returns to its former shape when released. In some instances, a spring can be shaped in an at least partially helical manner. Exemplary uses of a spring include exerting constant tension or absorbing movement.

As used herein, the term "appliance" can refer to a device designed to perform a specific task. For example, the specific task can be a dental task related where example apparatuses can include mouthguards, retainers, crowns, or the like. The term "apparatus" may be used interchangeably with the term "appliance".

As used herein, the term "wireless" can refer to the use of radio waves, microwaves, or the like (as opposed to wires or cables) to exchange (e.g., transmit and/or receive) signals.

As used herein, the term "wireless transceiver" can refer to a hardware element that can facilitate the exchange (e.g., transmission and/or reception) of signal embodied within radio waves, microwaves, or the like.

As used herein, the term "non-invasive" can refer to a medical procedure or medical device that does not require the opening of a subject's body and/or the introduction of medical instruments into the body.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to obstructive sleep apnea (OSA) and, more specifically, to systems and methods for OSA detection and monitoring. OSA can be characterized by recurrent airway obstructions during sleep. The airway obstructions can be due to soft tissue collapsing into the oropharynx, such as sleep-induced relaxation of throat and/or tongue muscles. OSA can be detected and monitored by tracking movement of a subject's tongue during sleep to determine the amount and duration of airway obstructions that are indicative of OSA.

A non-invasive oropharynx appliance can be coupled to a sensing system. The oropharynx appliance can be adapted to prevent the pharyngeal portion of the tongue from collapsing. The oropharynx appliance can include a passive tongue retention structure having an end portion adapted to prevent the pharyngeal portion of the tongue from collapsing and at least one anchoring structure adapted to secure the passive tongue retention structure within the subject's mouth in a removable fashion. The oropharynx appliance can also be coupled to one or more sensors of the sensing system to detect properties indicative of OSA. The one or more sensors can be arranged at various positions on the oropharynx appliance. For example, the one or more sensors can include a sensor to detect movement of a portion of the tongue into the oropharynx, an air flow sensor, a force sensor, an oxygen saturation ($SaO_2$) sensor, an electrocardiogram (ECG) sensor, a temperature sensor, and/or a sound sensor. The oropharynx appliance can also be coupled to a wireless transceiver (e.g., including a wireless transmitter and/or a wireless receiver) to transmit data recorded by the one or more sensors to a remote diagnostic device.

III. Systems

One aspect of the present disclosure, as shown in FIG. 1, can include a system 10 that detects and monitors obstructive sleep apnea (OSA). OSA can be characterized by recurrent airway obstructions during sleep due to soft tissue collapsing into the oropharynx. The system 10 can include a sensing system 14 that can track movement of a subject's tongue during sleep to determine the amount and duration of airway obstructions that are indicative of OSA. The sensing system 14 can also detect additional parameters indicative of OSA, such as air flow, force, oxygen saturation ($SaO_2$), electrocardiogram (ECG), temperature, and/or sound/vibration.

At least a portion of the sensing system 14 can be attached to or integrated within the oropharynx appliance 12. The oropharynx appliance 12 and at least a portion of the sensing system 14 can be adapted for insertion into a subject's mouth. The oropharynx appliance 12 can be an at least partially non-invasive solution to maintain airway patency during sleep. In other words, the system 10 can be configured for placement into a subject's mouth during sleep—at night and/or during the day. For example, the system 10 can be placed in the subject's mouth at a sleep lab or at home. At least a portion of the oropharynx appliance 12 can be fitted to or constructed for at least a portion of the subject's mouth. In some instances, the oropharynx appliance 12 can be fitted tightly within the subject's mouth (e.g., to the subject's lower teeth) so that the oropharynx appliance 12 does not dislodge when placed into the subject's mouth before, during, or after sleep.

The oropharynx appliance 12 can employ a mechanical design that is configured to prevent airway occlusion during sleep. The mechanical design prevents the undesired collapse of soft tissue into the oropharynx, thereby maintaining airway patency. In some instances, the soft tissue can be the tongue. Muscles of the tongue relax during sleep, causing tissue of the tongue to be pulled into the oropharynx by negative pressure generated during inspiration and obstruct the airway. The mechanical device can prevent the tongue from moving backwards into the oropharynx during inspiration and obstructing the airway. Although an oropharynx appliance that can be situated behind the tongue in the oropharynx will be described throughout, it will be noted that other placements for the oropharynx appliance 12 can be used, such as behind the soft palate in the nasopharynx. The oropharynx appliance 12 need not be behind the tongue and, instead may be in any position that is adapted to prevent the pharyngeal portion of the tongue from collapsing. The sensing system 14 can detect and monitor instances of the collapse of the pharyngeal portion of the tongue indicative of OSA that are restrained by the oropharynx appliance 12.

Figure 2:
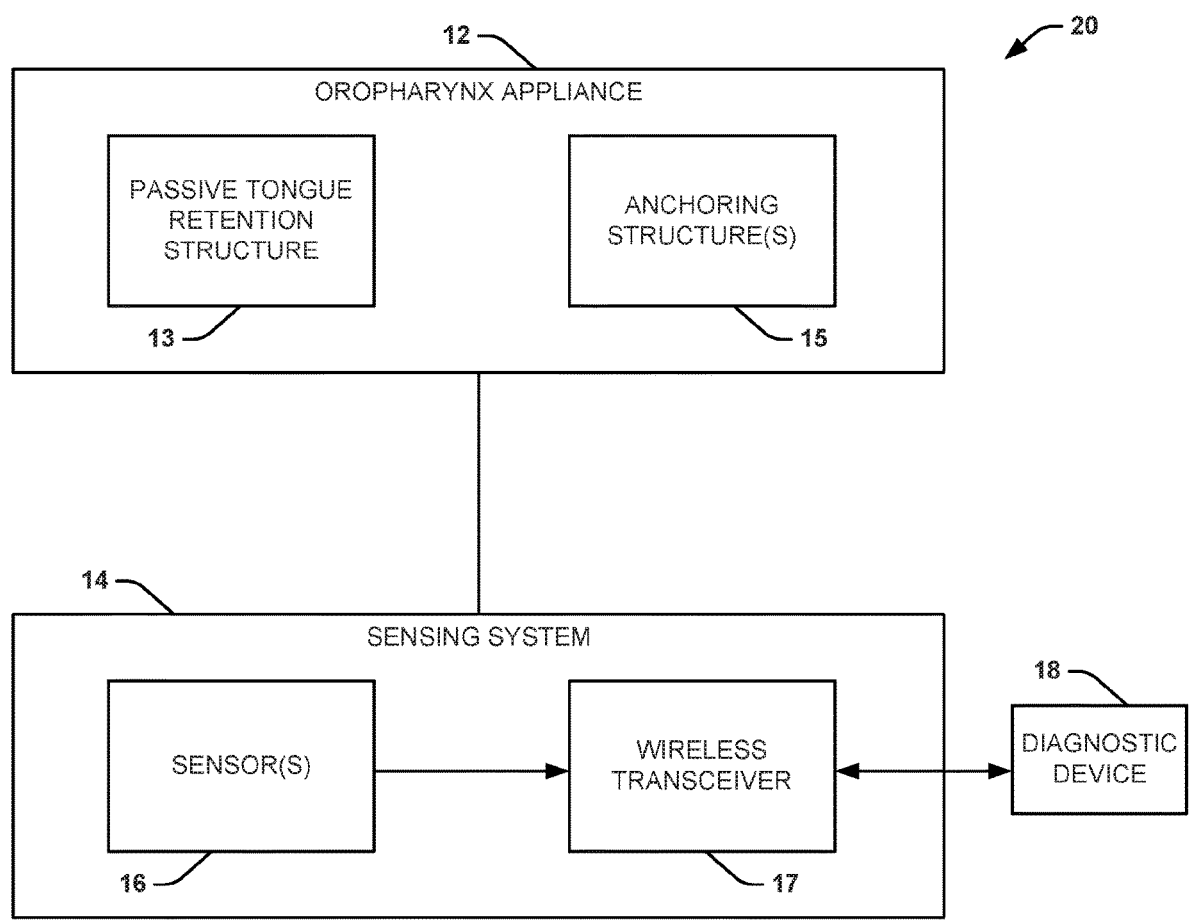
FIG. 2 is an illustration of an example of the system of FIG. 1 in communication with a remote diagnostic device.

FIG. 2 illustrates a system 20 that includes the oropharynx appliance 12 attached to and/or integrated with the sensing system 14. The oropharynx appliance 12 and the sensing system 14 can be integrated as a standalone device, in some instances. The sensing system 14 can include one or more sensors 16 that can record data and send the data to a wireless transceiver 17. The wireless transceiver 17 can send the data to an external diagnostic device 18. The external diagnostic device 18, in some instances, can be remote from the sensing system 14. The external diagnostic device 18 can be associated with the subject (e.g., a mobile phone, tablet computer, PDA, laptop computer, desktop computer, or the like). The external diagnostic device 18 associated with the patient can send the data to a device associated with a physician for diagnosis and/or monitoring. The system 20 can be used for long term monitoring of OSA. In other instances, the system 20 can be used for compliance monitoring to determine whether the subject is using a prescribed OSA prevention device.

The sensing system 14 can include one or more sensors 16. For example, one of the sensors can track movement of a subject's tongue during sleep to facilitate the determination of the amount and duration of airway obstructions that are indicative of OSA. Data related to the tracking of the movement of the tongue can be transmitted to the diagnostic device 18, which can analyze the data, which may lead to the detection, diagnosis, and/or monitoring of obstructive sleep apnea (OSA). The sensors 16 can also include one or more of an air flow sensor, a force sensor, an oxygen saturation ($SaO_2$) sensor (e.g., a plethysmograph, a light emitting diode, a photoresistor, etc.), an electrocardiogram (ECG) sensor (e.g., sensing electrodes, a reference electrode, and an amplifier), a temperature sensor, and/or a sound/vibration sensor (e.g., a passive microphone, a piezoelectric sensor, a vibration sensor, etc.). The sensors 16 can be located at different parts of the oropharynx appliance 12. For example, the sensors 16 can be located at specific parts of the passive tongue retention structure 13 and/or the anchoring structure 15.

In some instances, the sensors 16 can include a force sensor. For example, the force sensor can be configured to measure a force associated with movement of the passive tongue retention structure 13. The force can be used to measure a position of the pharyngeal portion of the tongue to detect an obstruction of the oropharynx. In some instances, the force sensor can include a force transducer to directly measure the force associated with movement of the passive tongue retention structure 13. In other instances, the force sensor can include a displacement sensor to measure the force indirectly without a force transducer. The displacement sensor can be, for example, a capacitive sensor, a resistive sensor, or an inductive sensor. One type of displacement sensor that may be especially useful is a linear variable displacement transducer (LVDT). When the sensor 16 is a displacement sensor and the at least one anchoring structure 15 includes at least one spring portion, the force, F, associated with the passive tongue retention structure can be determined by the equation $F=kx$, where k is a spring constant of the at least one spring portion and x is the position (or displacement) of the posterior portion of the tongue. In some instance, the sensing system 14 can include one of more additional sensors 16 to measure other properties related to the detection, diagnosis, and/or monitoring of OSA. One example additional sensor can be an air flow sensor that can measure air flow through the oropharynx. The air flow sensor can be located on an end portion of the passive tongue retention structure 13. For example, the air flow sensor can be included with the engagement device, when the engagement device is present. The additional sensors can include other sensors to detect $SaO_2$, EKG, temperature, or other properties that can contribute to the diagnosis of OSA. In other instances, the sensing system 14 can include a stimulation means that can be used to retrain muscles contributing to the obstruction to behave properly. The stimulation means can include at least one electrode located between 0 and 20 degrees from the end of the passive tongue retention structure 13. Through stimulation with an electrical waveform, the tongue can be activated to reflexively move forward and out of the obstructing position. The waveform can be configured to activate the tongue to move, but not to activate the oropharynx and not to cause pain.

The wireless transceiver 17 of the sensing system 14 can be configured to transmit data recorded by the sensor 16 to an external diagnostic device 18. In some instances, the wireless transceiver 17 can also be configured to receive signals from an external device. For example, portions of the system 10 can be powered externally and the wireless transceiver 17 can receive the power signal. The wireless transceiver 17 can be configured for short range and/or long-range transmission. For example, when the external diagnostic device 18 is located in the same room as the wireless transceiver 17, the wireless transceiver 17 can transmit the data from the sensor 16 to the external diagnostic device 18 according to a short-range wireless protocol (e.g., Bluetooth, Zigbee, or the like). However, when the external diagnostic device 18 is located outside of the same room as the wireless transceiver 17, the wireless transceiver 17 can transmit the data from the sensor 16 to the external diagnostic device 18 according to a long range wireless protocol (e.g., Wi-Fi, cellular, or the like). In either situation, the external diagnostic device 18 can be a smartphone, a tablet computing device, a laptop computer, a desktop computer, one or more servers, or the like.

The external diagnostic device 18 can receive the data from the sensor 16 and analyze the data to determine whether the subject exhibits characteristics of OSA, which can lead to the diagnosis of OSA. Information garnered from the data can be used to generate an OSA prevention device. The weight of the tongue can be estimated and a force required to prevent the tongue from falling into the throat can be estimated or calculated based on the displacement measurement and the k-constant of the spring. An OSA appliance can be fabricated that provides the force required to prevent the tongue from falling into the throat. The analysis performed by the external diagnostic device 18 can include a calibration procedure in which the data is normalized relative to a location of a reference point (e.g., the top of an incisor tooth). It is then possible to determine the distance between the back of the tongue (or the position of the portion of the passive tongue retention structure 13) and a known position of the dorsal wall of the oropharynx. If this distance is near zero, then a complete occlusion has occurred. The amount of time for which the occlusion occurs can also be calculated. In some instances, at least a portion of this determination can occur in the sensing system 14. In other instances, the external diagnostic device 18 can receive sensed data from the sensing system 14 and determine that the oropharynx appliance 12 is no longer working (e.g., positioned correctly). The diagnostic device 18 can display a warning indicating that the oropharynx appliance 12 is no longer working correctly as a visual message on a display, as an audio message from a speaker, as a tactile message through vibration, or the like.

Figure 3:
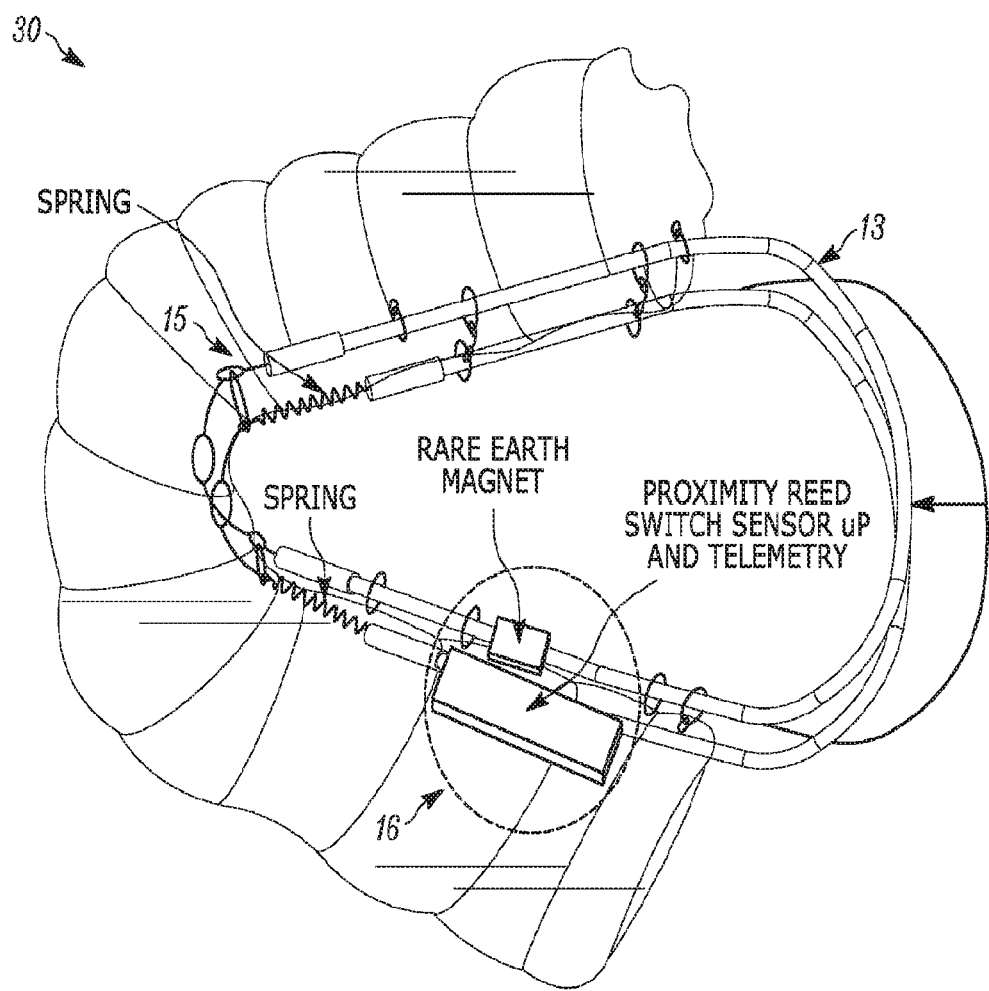
FIG. 3 is a photograph of another example of the system of FIG. 1.

FIG. 3 is a photograph showing another example 30 implementation of the system 10 or 20 with a passive tongue retention structure 13 attached to a mouthguard 15 configured for the lower jaw with springs and loops. It should be noted that FIG. 3 presents just one possible implementation to detect, monitor, and/or diagnose sleep apnea in a patient, to detect compliance for insurance purposes, and/or to detect effective use when no obstruction is present. The mouthguard 16 can be a different type of dental device that can be used to anchor the passive tongue retention structure 13, such as a hook, a mouth guard, a retainer, a crown, or the like. However, in some instances, the dental appliance is not needed at all and, instead, the passive tongue retention structure 13 can be anchored by a device that is at least partially within the oropharynx appliance, such as a spring, a loop, or a hook. The oropharynx appliance 12 can also include other anchoring means, such as one or more magnets, hydraulics, electrostatics, or the like.

Additional features can include a tube that holds the spring and/or the wire placed inside the mandible, further components to allow for better engagement of the tongue, and/or a spring-loaded telescoping system to eliminate the spring. In use, the system can be placed in the subject's mouth at night like a regular mouth guard. The system is fitted to the subject's mouth and fits tightly onto the lower teeth. The system can prevent any obstruction during sleep while the tongue muscles are relaxed from the lack of muscle tone. The natural movement of the tongue into the oropharynx can be prevented by the springs that resist the tongue's weight. Thus, in some instances, the spring specifications can be adjusted to the subject's tongue mass so that the subject can swallow any saliva generated at any time. The system can be removed in the morning and cleaned with methods similar to those used for false teeth. The system 10 allows a preset clearance of about 5-10% of the maximum distance between the wire and the teeth.

As shown in FIG. 3, the sensors 16 can include a permanent magnet that is attached to the wire and a proximity sensor (reed switch) that closes when the magnet indicates an obstruction. Upon closure of the reed switch, signals are transmitted by telemetry to an external diagnostic device 18. Additionally, the circuit elements of the system 10 are also powered externally. Alternatively, a linear variable displacement transducer (LVDT) can be substituted for the sensor 16 to record the displacement. A microprocessor samples the displacement (x) and calculates the force (F) based on the spring constant (k).

As shown in FIG. 2, the oropharynx appliance 12 can include a passive tongue retention structure 13 and at least one anchoring structure 15. In one aspect, the passive tongue retention structure 13 can be primarily constructed of a thin wire (made of metal, polymer, organic material, or the like) that is stiff enough to prevent bending by the tongue. For example, the thickness of the wire can be nonconstant. Additionally, the wire can have a circular, curved, rectangular, linear, curvilinear, star, flat, or any other shaped cross section. The wire can be biocompatible to minimize irritation in the patient's mouth. Additionally, the wire can be durable and/or robust so that portions of the wire do not dislodge while the subject is sleeping. For example, the wire can be constructed of a metal, organic material, and/or polymer that is itself biocompatible or coated with a biocompatible material. The end portion of the passive tongue retention structure 13 can be constructed of the same wire or a different biocompatible material.

For example, as an alternative to FIG. 2, the oropharynx appliance 12 can be configured identically or similarly to any one of the configurations shown in FIGS. 4-14. Any one of the oropharynx appliances 12 shown in FIGS. 4-14 can interface with a removable and/or permanent dental device (like a hook, a mouth guard, a retainer, a crown, or the like) to anchor to a subject's mouth. However, the oropharynx appliance does not need the dental devices and can instead be anchored by a device that is at least partially within the oropharynx appliance, such as a spring, a loop, or a hook. The oropharynx can also include other anchoring means, such as one or more magnets, hydraulics, electrostatics, or the like. The sensing system 14 can be located at any part of the oropharynx appliances 2 shown in FIGS. 4-14 and/or in the accompanying dental device.

FIG. 4 shows an example of a mechanical device, shown and described herein as an oropharynx appliance 12, including a passive tongue retention structure 13 and an anchoring structure 15 that holds the passive tongue retention structure 13 in the subject's mouth. The oropharynx appliance 12 can extend from an anchor point (a tooth, as shown, or another area such as a portion of the gum, the tongue, or any other desired anchor point), along a lingual surface of the mandible and/or over the top surface of the tongue, and ultimately, behind at least a portion of the pharyngeal portion of the subject's tongue to prevent the portion of the tongue from collapsing into the throat.

In some instances, the passive tongue retention structure 13 can be maintained within a plane that is parallel with the mandible. In still other instances, the passive tongue retention structure 13 can extend over the surface of the tongue. In still other instances, the tongue retention structure can extend over, under, or around the tongue in any configuration as long as at least a portion of the passive tongue retention structure 13 extends behind at least a portion of the pharyngeal portion of the subject's tongue to prevent the pharyngeal portion of the tongue from collapsing into the throat. However, the passive tongue retention structure 13 need not be behind the tongue and, instead may be in any position that is adapted to prevent the pharyngeal portion of the tongue from collapsing.

The oropharynx appliance 12 subject to several design considerations. The passive tongue retention structure 13 must prevent the tongue from moving backwards into the oropharynx, while also allowing movement of the tongue for swallowing. However, at least a portion of the passive tongue retention structure 13 must allow movement of the tongue, but prevent the passive tongue retention structure 13 from moving upwards or downwards into the oral cavity or oropharynx. Additionally, the portion of the passive tongue retention structure 13 must not generate a gag reflex and must not generate a significant amount of saliva (e.g., more than normally generated without the oropharynx appliance 12).

In one aspect, the passive tongue retention structure 13 can be primarily constructed of a thin wire (made of metal, polymer, an organic material, or the like) that is stiff enough to prevent bending by the tongue. For example, the thickness and/or cross-sectional area of the wire can be nonconstant. Additionally, the wire can have a circular, curved, rectangular, linear, flat, curvilinear, or any other shaped cross section. The wire can be biocompatible to minimize irritation in the patient's mouth. Additionally, the wire can be durable and/or robust so that portions of the wire do not dislodge while the subject is sleeping. The wire can, in some instances, be constructed of a metal and/or polymer that is itself biocompatible or coated with a biocompatible material. As an example, the wire can have a ribbon-like form with a flat direction facing the tongue and the cheeks with at least one wiggle through the length (this eliminates the need for the spring shown in FIG. 5). The passive tongue retention structure 13 can include an end portion 22 that can be constructed of the same wire or a different biocompatible material. For example, the end portion can be arcuate.

In another aspect, the end portion 22 can be adapted to restrain all or at least a portion of the subject's tongue. The passive tongue retention structure 13 can be sized and dimensioned so that the end portion 22 prevents the posterior pharyngeal portion of the tongue from obstructing the subject's oropharynx during sleep, without triggering the gag reflex, while still permitting the tongue to move during swallowing. In some instances, the end portion 22 can include at least a rounded portion. In other instances, the end portion 22 can include one or more bends.

As shown in FIG. 6, the end portion 22 can include an engagement structure 42 that is configured to establish contact with the posterior pharyngeal portion of the tongue. In some instances, the engagement structure 42 can be larger than the rest of the passive tongue retention structure 13 to prevent the tongue from obstructing the oropharynx. For example, the engagement structure 42 can be in the form of: one or more wire coils of the same or different biocompatible material as the wire of the passive tongue retention structure 13; an additional portion of the same or different wire attached to the passive tongue retention structure 13; and/or a piece of material either the same as the wire or different from the wire. The engagement structure 42 can provide an additional portion to prevent the tongue from moving backwards into the oropharynx during inspiration and obstructing the airway, while not generating the gag reflex and not generating an excess amount of saliva.

The anchoring structure 15 can be adapted to secure the passive tongue retention structure 13 to at least one of the subject's teeth or a portion of the subject's mandible in a removable fashion. For example, the anchoring structure 15 can include one or more loops to secure the oropharynx appliance 12 to one or more teeth and/or portions of the mandible. In another example, the anchoring structure 15 can include a magnet configured to attach to a reciprocal magnetic member that is connected to a portion of the subject's mouth. In some instances, as shown in the oropharynx appliance 12 of FIG. 5, the anchoring structure 15 can include one or more springs 32. The one or more springs 32 can be configured to allow movement of the tongue for swallowing. Although illustrated separately, it will be appreciated that, in some instances, the one or more springs 32 and the engagement structure 42 can be used together in another example of the oropharynx apparatus of the present disclosure.

FIG. 7 shows an alternative configuration of an oropharynx appliance 12, in which the passive tongue retention structure 13 loops or bends back to the anchoring structure 15, increasing the strength of the passive tongue retention structure. In other words, the oropharynx appliance 12 can extend from an anchor point, along a lingual surface of the mandible, behind at least a portion of the posterior pharyngeal portion of the subject's tongue to contact the posterior pharyngeal portion of the subject's tongue, and then extend back along the lingual surface of the mandible, to again contact the anchor point. In some instances, the passive tongue retention structure 13 can stay within a plane that is parallel with the mandible. In other instances, the portion of the passive tongue retention structure 13 can run over an upper surface of the tongue.

The oropharynx appliance 12 of FIG. 7-9, is subject to several design considerations. The passive tongue retention structure 13 must prevent the tongue from moving backwards into the oropharynx, while also allowing movement of the tongue for swallowing. However, at least a portion of the passive tongue retention structure 13 must be attached so that movement of the tongue does not bring the passive tongue retention structure 13 upwards or downwards into the oral cavity or oropharynx. For example, the portion of the passive tongue retention structure 13 can remain in line with one or more of the subject's lower incisive teeth. Additionally, the portion of the passive tongue retention structure 13 must not generate a gag reflex and must not generate a significant amount of saliva (e.g., more than normally generated without the oropharynx appliance 12).

In the oropharynx appliance 12 of FIG. 7, the thickness, cross-sectional shape, and/or stiffness of the passive tongue retention structure 13 must be well controlled to hold the tongue so that the tongue does not block the oropharynx while preventing a gag reflex, preventing the formation of excess saliva, and allowing movement of the tongue for swallowing.

FIG. 8 shows a further example of an oropharynx appliance 12 that can include two or more springs 32a and 32b. The two or more springs 32a and 32b can allow greater movement of the tongue for swallowing and stronger attachment of the passive tongue retention structure 13 to the anchoring structure 15. FIG. 9 shows a further example of an oropharynx appliance 12 that can include an engagement structure 42. Although the two or more springs 32a and 32b and the engagement structure 42 are illustrated as being used separately, it will be appreciated that the two or more springs 32a and 32b and the engagement structure 42 can be used together in the same oropharynx protection appliance. However, as an example, to eliminate the need for the springs 32a, 32b, the passive tongue retention structure 13 can have a ribbon-like form with a flat direction facing the tongue and the cheeks with at least one wiggle through the length.

Figure 10:
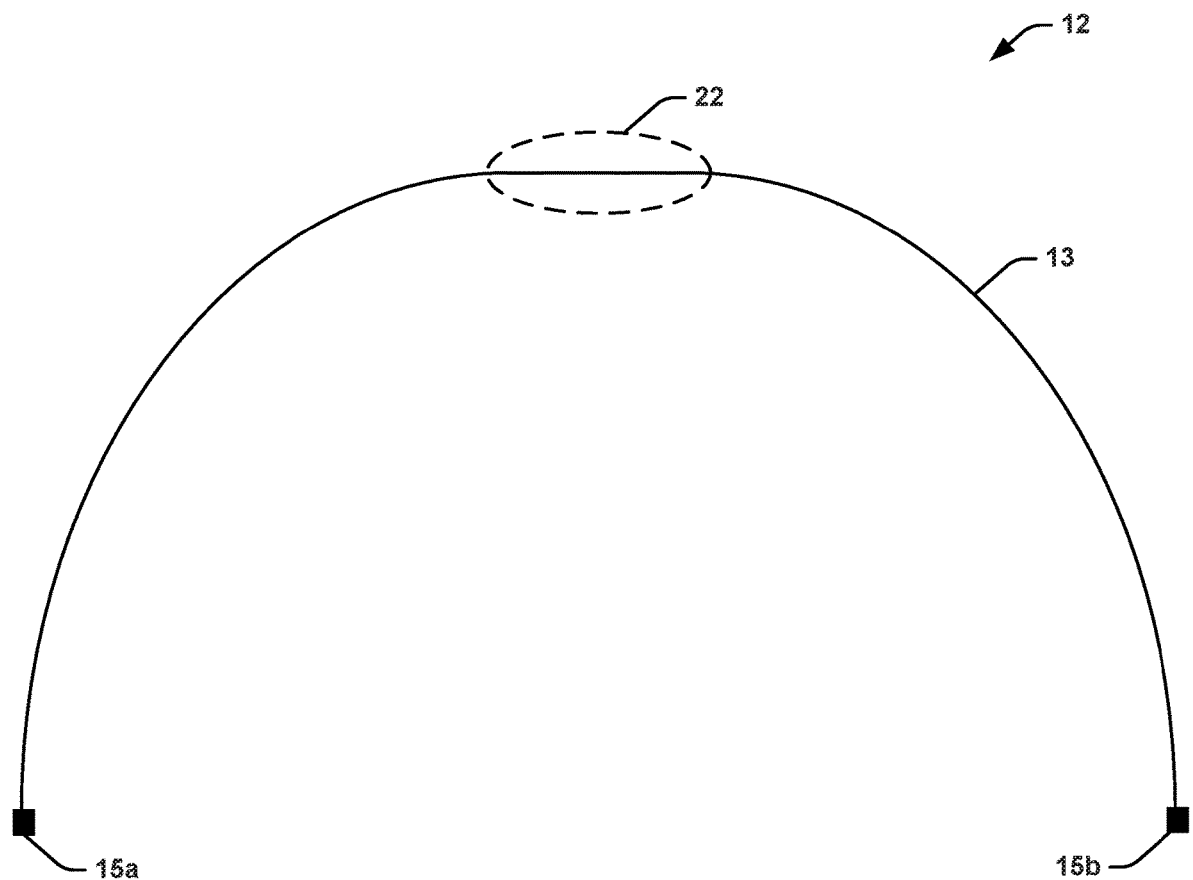

FIG. 10 shows an alternative configuration of an oropharynx appliance 12 in which the passive tongue retention structure 13 includes a portion (end portion 22) adapted to prevent the pharyngeal portion of the tongue from collapsing. The passive tongue retention structure 13 extends between bilateral anchoring structures 15a and 15b. The anchoring structures 15a and 15b can attach the passive tongue retention structure 13 to one or more teeth located bilaterally on the subject's lower jaw. However, at least one of the anchoring structures 15a and 15b can attach to a portion of the subject's lower jaw itself. Alternatively, at least one of the anchoring structures 15a and 15b can attach to a portion of the subject's tongue.

In some instances, the passive tongue retention structure 13 can stay within a plane that is parallel with the mandible. In other instances, a portion of the passive tongue retention structure 13 can extend over the top of the tongue. In further instances, the tongue retention structure can extend over, under, or around the tongue in any configuration as long as a portion of the passive tongue retention structure 13 prevents a pharyngeal portion of a tongue of a subject from collapsing.

The oropharynx appliance 12 of FIGS. 10-14 is subject to several design considerations. The passive tongue retention structure 13 must prevent the tongue from moving backwards into the oropharynx, while also allowing movement of the tongue for swallowing. However, at least a portion of the passive tongue retention structure 13 must prevent movement of the tongue from bringing the passive tongue retention structure 13 upwards or downwards into the oral cavity or oropharynx. For example, the portion of the passive tongue retention structure 13 can remain in line with one or more of the subject's lower incisive teeth. However, the passive tongue retention structure 13 is not required to be in line with the subject's lower incisive teeth. Additionally, the portion of the passive tongue retention structure 13 must not generate a gag reflex and must not generate a significant amount of saliva (e.g., more than normally generated without the oropharynx appliance 12) when preventing the portion of the pharyngeal portion of the tongue from collapsing into the oropharynx. For example, the passive tongue retention structure 13 can be of a thin, stiff wire with examples similar to that described with respect to FIG. 4.

Figure 11:
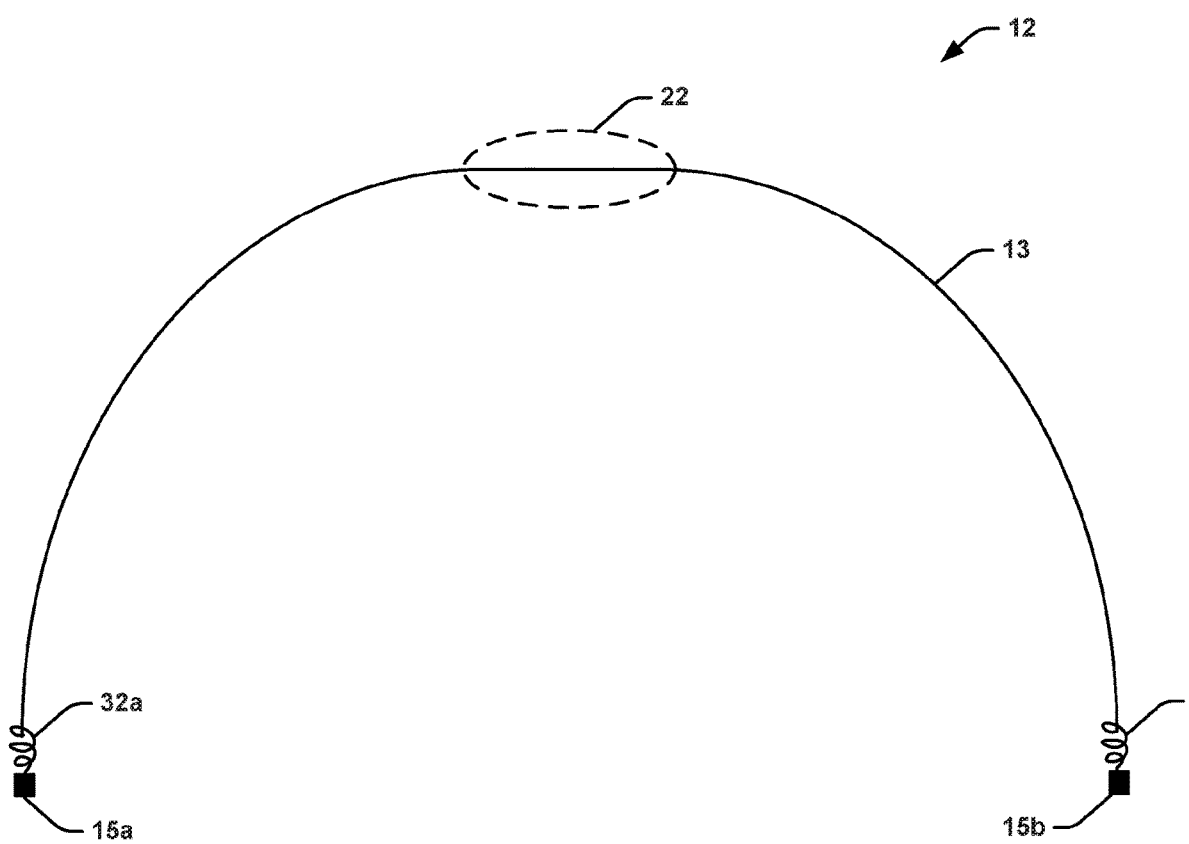
Figure 12:
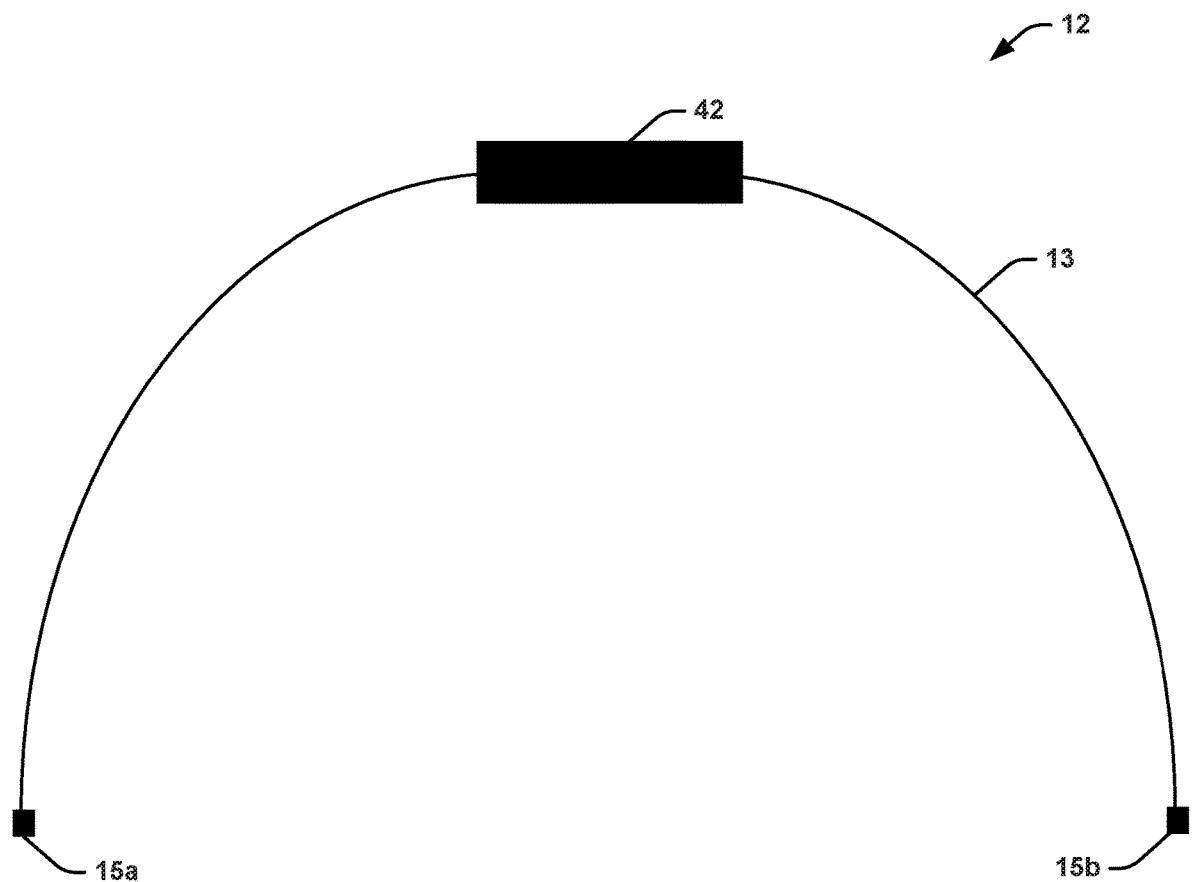

In one aspect, each anchoring structure 15a and 15b (FIG. 10) can be adapted to secure the passive tongue retention structure 13 to at least two of the subject's teeth and/or portions of the subject's mandible in a removable fashion. For example, the anchoring structure 15a and 15b can each include one or more loops to secure the oropharynx appliance 12 to the two or more teeth, portions of the gum, portions of the tongue, and/or portions of the mandible. In another example, the anchoring structure 15a and 15b can include magnets configured to attach to a reciprocal magnetic member that is connected to a portion of the subject's mouth. In some instances, the oropharynx appliance 12, as shown in FIG. 11, can include one or more springs 32a and 32b extending from the anchoring structures 15a and 15b. Although one spring 32a or 32b is shown as part of one anchoring structure 15a and 15b, two or more springs can be attached to each anchoring structure 15a and 15b to allow for greater movement of the tongue for swallowing and a stronger attachment of the passive tongue retention structure 13 to the anchoring structures 15a and 15b.

Figure 13:
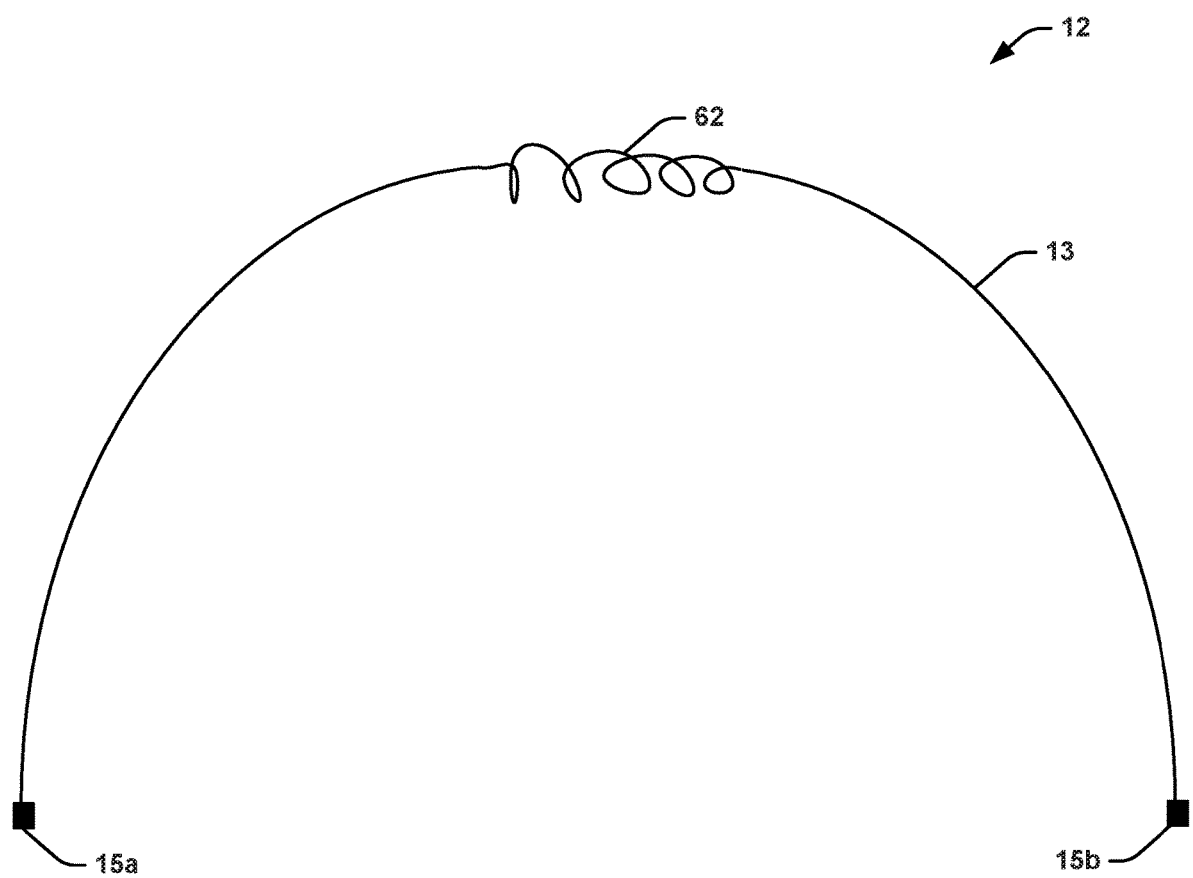
Figure 14:
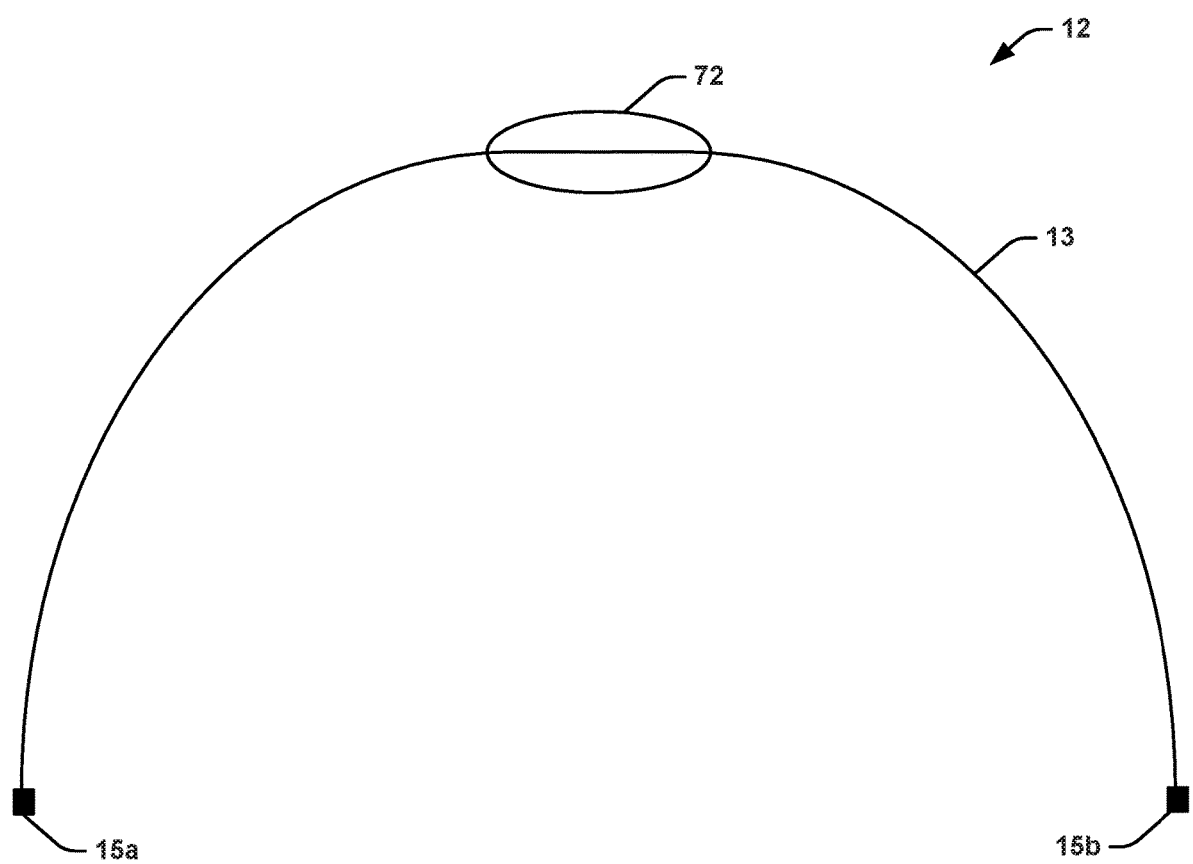

In another aspect, the end portion 22 can be adapted to contact a posterior pharyngeal portion of the subject's tongue. The passive tongue retention structure 13 can be sized and dimensioned so that the end portion 22 prevents the posterior pharyngeal portion of the tongue from obstructing the subject's oropharynx during sleep, without triggering the gag reflex, while still permitting the tongue to move during swallowing. As shown in the oropharynx appliance 12 of FIG. 12, the end portion 22 can include an engagement structure 42 that is configured to establish contact with the posterior pharyngeal portion of the tongue. In some instances, the engagement structure 42 can have a cross-sectional area larger than the rest of the passive tongue retention structure 13 to prevent the tongue from obstructing the oropharynx. For example, the engagement structure 42 can be in the form of one or more wire coils 62, as shown in FIG. 13. The engagement structure 42 can be of the same or different biocompatible material as the wire of the passive tongue retention structure 13. As a further example, the engagement structure 42 can be an additional portion of the same or different wire attached to the passive tongue retention structure 13. In another example, the engagement structure 42 can include a piece of material 72, FIG. 14, either the same as the wire or different from the wire. The engagement structure 42 can provide an additional surface area to prevent the tongue from moving backwards into the oropharynx during inspiration and obstructing the airway, while not generating the gag reflex and not generating an excess amount of saliva. The engagement structure 42, in some instances, can be used in combination with the springs 32a and 32b in an oropharynx appliance.

As an example, the passive tongue retention structure 13 need not be straight, as illustrated. Instead, the passive tongue retention structure 13 can be bent caudally by a small amount. Additionally, use of one or more springs 32a, 32b can be replaced by two earth magnets sliding into a groove. Moreover, the device need not contact the back of the tongue if one or more magnets are implanted in the tongue.

Figure 15:
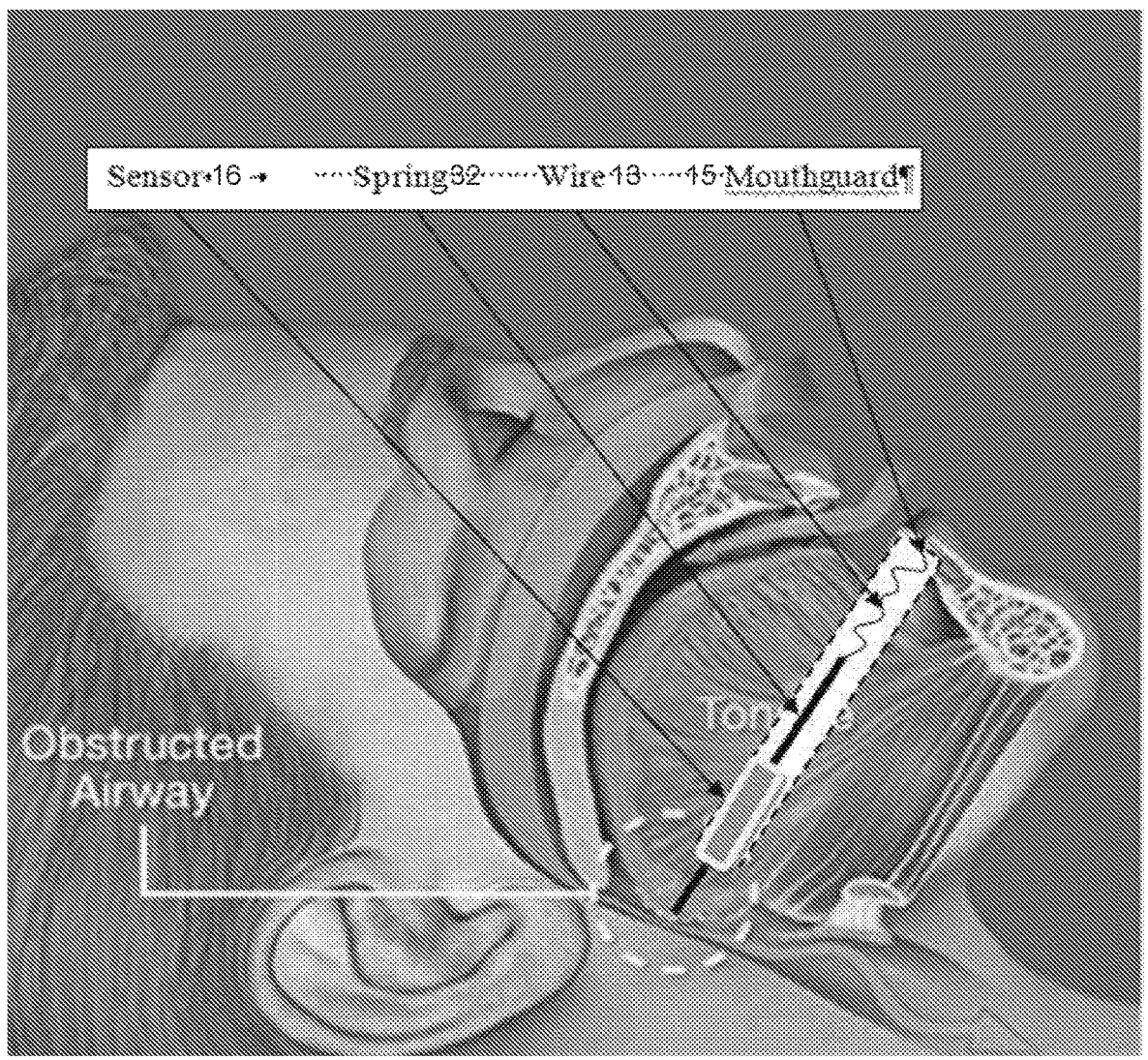
FIG. 15 is a side view illustration showing an example of the system of FIG. 1 being used in a subject's mouth during sleep to detect OSA.

FIG. 15 is a side view illustration showing an example of the system of 10 or 20 being used in a subject's mouth during sleep to detect, diagnose, and/or monitor OSA. In this example, the passive tongue retention structure 13 is made of a thin, stiff wire (made of an organic material, a polymer material, a metal, or the like) and the anchoring structure 15 includes a mouthguard or other dental appliance. In some examples, the mouthguard can be 3D-printed from a cone beam computer tomography (CBCT) obtained for the patient from a dentist's office. The design of the oropharynx appliance 12 can then be determined from the CBCT.

In constructing the oropharynx appliance 12, the wire is chosen to be very stiff in order to prevent bending by the tongue movement during swallowing. The wire is very thin to minimize the amount of saliva production and to minimize the gag reflex. The wire is attached to the mouthguard by a spring 32 and a displacement sensor 16. The wire is designed to wrap around the tongue, following the mandible, into the oropharynx. The spring allows movement of the tongue forward for swallowing. The displacement sensor 16 measures movement of the tongue. For example, as the tongue is falling into the oropharynx during an obstruction event, the displacement sensor 16 detects the displacement of the tongue (x). Once the obstruction event is terminated, the tongue will move back to its normal resting place.

Figure 16:
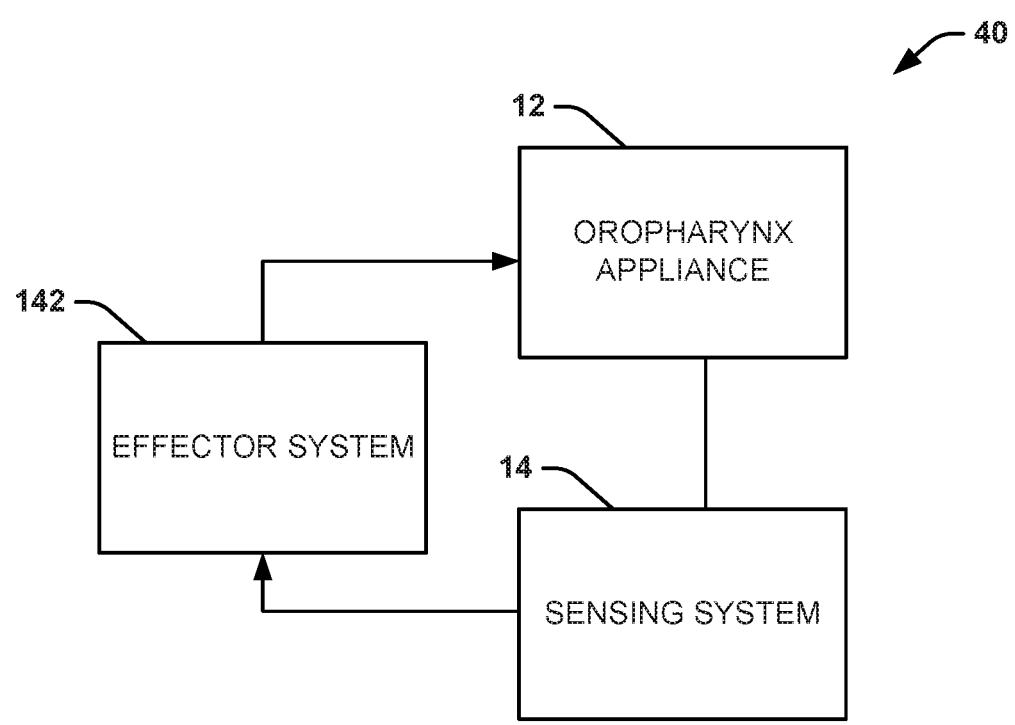
FIG. 16 an illustration of an example of the system of FIG. 1 as a closed loop.

FIG. 16 shows an example closed loop system 40, which includes the oropharynx appliance 12, the sensing system 14, and the external diagnostic device, which can be an effector system 142 that communicates with the sensing system 14 and the oropharynx appliance 12. The effector system 142 can deliver a signal to the oropharynx appliance 12 in response to the data from the sensing system 14. For example, the effector system 142 can deliver a pulse of electricity (or other signal that causes reflexive tightening of upper airway muscles) to the oropharynx appliance 12 for delivery to the tongue when a collapse is detected. This reflexive tightening can be used to train the tongue not to collapse into the oropharynx.

IV. Methods

Figure 17:
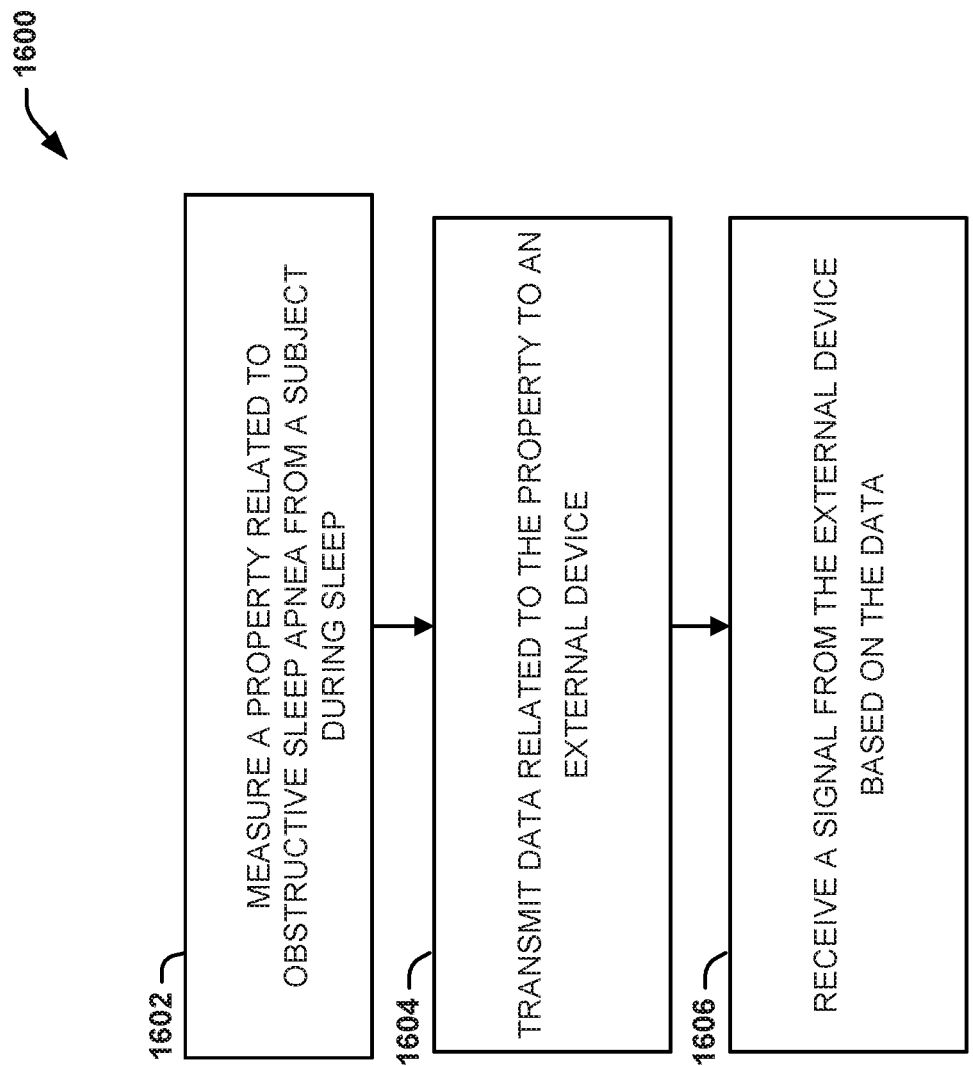
FIG. 17 is a process flow diagram showing an example of a method for OSA detection and monitoring, in accordance with another aspect of the present disclosure.
Figure 18:
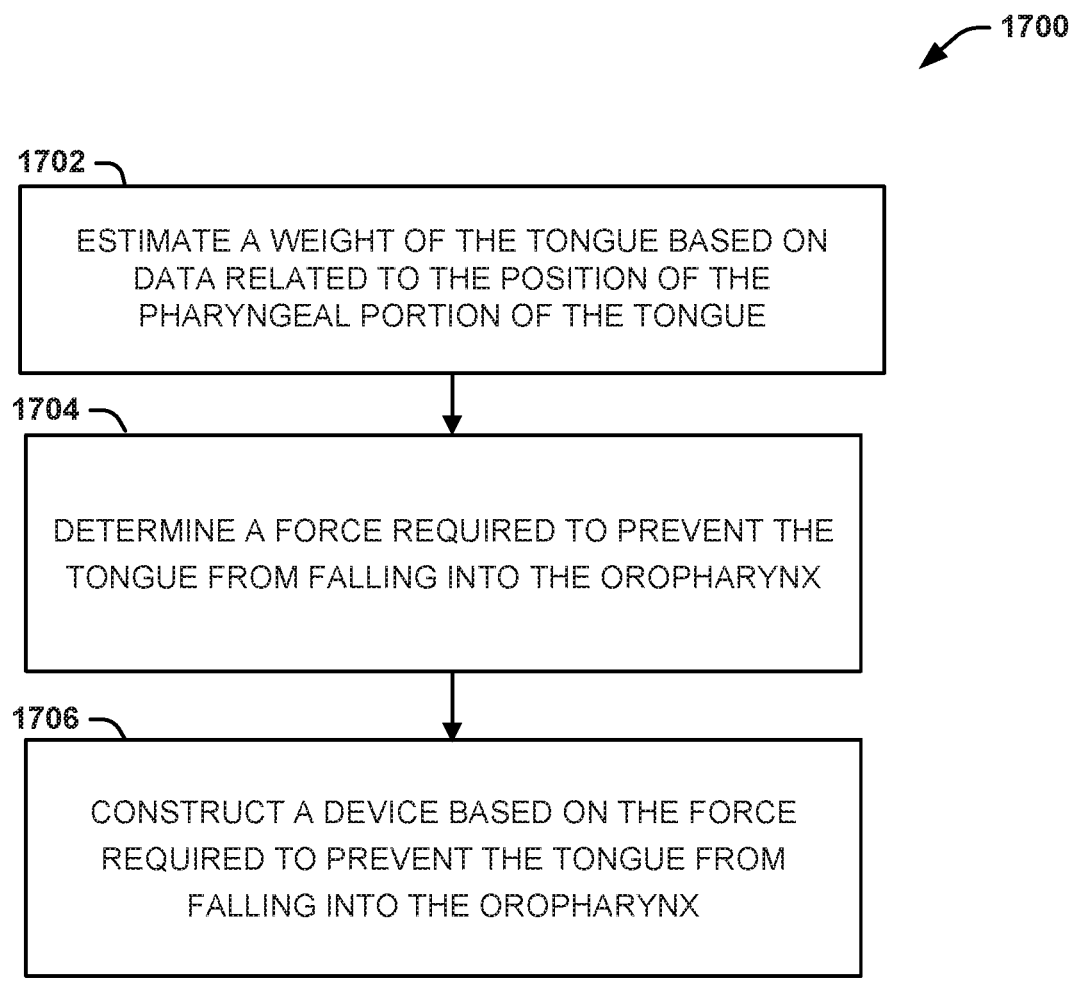
FIG. 18 is a process flow diagram showing an example of a method for constructing an OSA prevention device, in accordance with yet another aspect of the present disclosure.

Another aspect of the present disclosure can relate to methods for non-invasive direct monitoring, diagnosis, and treatment of obstructive sleep apnea (OSA). FIG. 17 shows an example of a method 1600 for OSA detection and monitoring. FIG. 18 shows an example of a method 1700 constructing an OSA prevention device.

The methods 1600 and 1700 are illustrated as process flow diagrams with flowchart illustrations. For purposes of simplicity, the methods 1600 and 1700 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 1600 and 1700.

FIG. 17 shows a method 1600 for OSA detection and monitoring. As an example, the method 1600 can be accomplished using the system 10 of FIG. 1 or the examples shown in FIGS. 2-16. At least a portion of the oropharynx appliance 12 can be fitted to or constructed for at least a portion of the subject's mouth. In some instances, the oropharynx appliance 12 can be fitted tightly within the subject's mouth (e.g., to the subject's lower teeth) so that the oropharynx appliance 12 does not move when placed into the subject's mouth before, during, or after sleep.

At 1602, a property related to OSA can be measured (e.g., by one or more sensors 16 on an oropharynx appliance 12). The property can include one or more of movement of a portion of the tongue into the oropharynx, air flow, force, oxygen saturation ($SaO_2$), electrocardiogram (ECG), and/or sound. At 1604, data related to the property can be transmitted (e.g., by wireless transceiver 17) to an external device (e.g., diagnostic device 18). At 1606, a signal can be received from the external device (e.g., diagnostic device 18) based on the data.

FIG. 18 shows a method 1700 for constructing an oropharynx appliance to prevent or treat sleep apnea in the subject based on tracking data that tracks the position of the pharyngeal portion of a subject's tongue during sleep. The measurement can be made of the position of the posterior pharyngeal portion of the tongue relative to the oropharynx (e.g., a known position of the dorsal wall of the oropharynx). The measurement can include one or more recorded data related to the distance, spread apart by a known time interval. For example, when motion of the tongue is detected, a plurality of measurements can occur separated by a known time interval for a specified amount of time. The data related to the position of the posterior pharyngeal portion of the tongue can be transmitted (e.g., by wireless transceiver 17 of sensing system 14) to an external diagnostic device (e.g., diagnostic device 18). A degree of obstruction of the oropharynx can be determined (e.g., by diagnostic device 18) at one or more times during sleep based on the transmitted data. For example, the sensor can determine a displacement of the posterior pharyngeal portion of the tongue during sleep. To increase accuracy of the measurement, a calibration procedure can be performed based on a distance between a reference point in a mouth of the subject (e.g., the tip of a lower incisor tooth) and a normal (resting) position of the posterior pharyngeal portion of the tongue.

At 1702 a weight of the tongue can be estimated (e.g., by the diagnostic device 18) based on data related to the position of the posterior pharyngeal portion of the tongue. At 1704, a force required to prevent the tongue from falling into the oropharynx can be determined (e.g., by the diagnostic device 18). When the sensor (e.g., sensor 16) and the oropharynx appliance (e.g., oropharynx appliance 12) are coupled by a spring, a force, F, associated with the passive tongue retention structure can be determined by the equation F=kx, where k is a spring constant of the spring and x is the position of the posterior pharyngeal portion of the tongue. At 1706, a device (e.g., oropharynx appliance 12) can be constructed based on the force required to prevent the tongue from falling into the oropharynx.

From the above description, those skilled in the art will perceive improvements, changes and modifications. Such improvements, changes and modifications are within the skill of one in the art and are intended to be covered by the appended claims.

The following is claimed:

1. A system comprising:
    an oropharynx appliance comprising:
        a passive tongue retention structure having an arcuate end portion adapted to contact a pharyngeal portion of a tongue of a subject and prevent the pharyngeal portion of the tongue of the subject from collapsing; and
        at least one anchoring structure that is connected to the passive tongue retention structure and adapted to secure the passive tongue retention structure within the subject's mouth in a removable fashion, wherein the at least one anchoring structure comprises a dental appliance adapted to mate with the passive tongue retention structure with at least one spring portion attaching the at least one anchoring structure to the dental appliance, where a force, F, associated with the passive tongue retention structure is determined by the equation F=kx, where k is a spring constant of the at least one spring portion and x is a position of the pharyngeal portion of the tongue; and
    a sensing system attached to a portion of the oropharynx appliance apparatus, the sensing system comprising:
        a sensor to measure the position of the pharyngeal portion of the tongue to detect an obstruction of the oropharynx; and
        a wireless transceiver to transmit data related to the obstruction of the oropharynx to a remote diagnostic device,
        where in the sensor is attached to the at least one anchoring structure, and
        wherein at least a portion of the sensor is attached to the dental appliance.

2. The system of claim 1, wherein the sensor measures a force associated with movement of the passive tongue retention structure.

3. The system of claim 2, wherein the sensor comprises a displacement sensor to measure the force without a force transducer.

4. The system of claim 3, wherein the displacement sensor comprises a capacitive sensor, a resistive sensor, or an inductive sensor.

5. The system of claim 3, wherein the displacement sensor comprises a linear variable displacement transducer (LVDT).

6. The system of claim 2, wherein the sensor comprises a force transducer.

7. The system of claim 1, wherein the sensing system further comprises an air flow sensor to measure air flow through the oropharynx.

8. The system of claim 7, wherein the oropharynx appliance further comprises an engagement structure located on the end portion,
    wherein the air flow sensor is positioned with the engagement structure on the end portion of the passive tongue retention structure.

9. The system of claim 1, wherein the sensing system comprises another sensor configured to face a gum of the subject that detects oxygen saturation ($SaO_2$).

10. The system of claim 1, wherein the sensor comprises a piezoelectric sensor, a vibrational sensor, or a microphone sensor to detect snoring indicative of sleep apnea.

11. The system of claim 1,
    wherein the dental appliance comprises a mouthguard, a retainer, or a crown.

12. A method comprising:
    measuring, by a sensor of a sensing system attached to a portion of an oropharynx apparatus, a position of a pharyngeal portion of a tongue of a subject during sleep, wherein the oropharynx apparatus comprises:
        a passive tongue retention structure having an arcuate end portion adapted to contact a portion of a posterior of the pharyngeal portion of the tongue of the subject, and
        at least one anchoring structure that is connected to the passive tongue retention structure and adapted to secure the passive tongue retention structure to within the subject's mouth in a removable fashion and comprises a dental appliance adapted to mate with the passive tongue retention structure with a spring attaching the at least one anchoring structure to the dental appliance,
        wherein the sensor is attached to the at least one anchoring structure, and
        wherein at least a portion of the sensor is attached to the dental appliance, such that a force, F, associated with the passive tongue retention structure is determined by the equation F=kx, where k is a spring constant of the at least one spring portion and x is a position of the posterior of the pharyngeal portion of the tongue;
    transmitting, by a wireless transceiver of the sensing system, data related to the position of the pharyngeal portion of the tongue to an external diagnostic device; and
    determining, by the external diagnostic device, a degree of obstruction of the oropharynx of the subject at one or more times during sleep based on the transmitted data.

13. The method of claim 12, further comprising constructing an oropharynx appliance to prevent or treat obstructive sleep apnea based on the transmitted data.

14. The method of claim 13, wherein constructing the device further comprises:
    estimating a weight of the tongue based on the transmitted data;
    determining a force required to prevent the tongue from falling into the oropharynx; and
    constructing the device based on the force required to prevent the tongue from falling into the oropharynx.

15. The method of claim 12, wherein the sensor measures a displacement of the pharyngeal portion of the tongue during sleep.

16. The method of claim 15, further comprising calibrating the sensor based on a distance between a reference point in the mouth of the subject and a normal position of the pharyngeal portion of the tongue.

17. The method of claim 12, further comprising placing the oropharynx apparatus into the mouth of the subject before sleep, wherein the oropharynx apparatus is fitted tightly within the mouth.

* * * * *